United States Patent [19]

Potier et al.

[11] 4,305,875
[45] Dec. 15, 1981

[54] PROCESS FOR THE SYNTHESIS OF VINBLASTINE AND LEUROSIDINE

[75] Inventors: Pierre Potier, Bois d'Arcy; Pierre Mangeney, Paris; Nicole Langlois; Yves Langlois, both of Bures sur Yvette, all of France

[73] Assignee: Agence Nationale de Valorisation de la Recherche (ANVAR), Neuilly sur Seine, France

[21] Appl. No.: 100,551

[22] Filed: Dec. 5, 1979

[30] Foreign Application Priority Data

Dec. 8, 1978 [FR] France .................. 78 34599

[51] Int. Cl.³ .......................... C07D 519/04
[52] U.S. Cl. .............................. 260/244.4
[58] Field of Search ............ 260/244.4; 546/51; 424/258, 262

[56] References Cited

U.S. PATENT DOCUMENTS 4,144,237 3/1979 Kutney .................. 260/244.4

FOREIGN PATENT DOCUMENTS 2614863 10/1977 Fed. Rep. of Germany ... 260/244.4

OTHER PUBLICATIONS

Mangeney, et al., J. Am. Chem. Soc., vol. 101(8) pp. 2243–2245, 04/11/79.
Langlois, et al., Tetrahedron Letters, 1976, (14), pp. 1099–1102.
Kutney, et al., Canadian J. Chemistry, vol. 56, (1), pp. 62–70, 01/78.
Fieser, et al., Reagents for Organic Synthesis, Jon Wiley & Sons, Inc., New York, pp. 1150–1151 (1967).

Primary Examiner—Donald G. Daus
Assistant Examiner—Diana G. Rivers
Attorney, Agent, or Firm—Fleit & Jacobson

[57] ABSTRACT

The invention provides a process for the preparation of leurosidine or vinblastine, which comprises hydroxylating and reducing $\Delta^{20'}$ dehydroxy-20' vincaleucoblastine corresponding to formula (II):

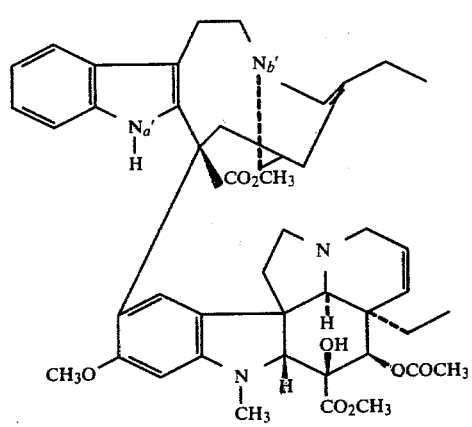

II

10 Claims, No Drawings

PROCESS FOR THE SYNTHESIS OF VINBLASTINE AND LEUROSIDINE

This invention relates to a process for the preparation of leurosidine and vinblastine.

Leurosidine and vinblastine are represented by the general formula (I):

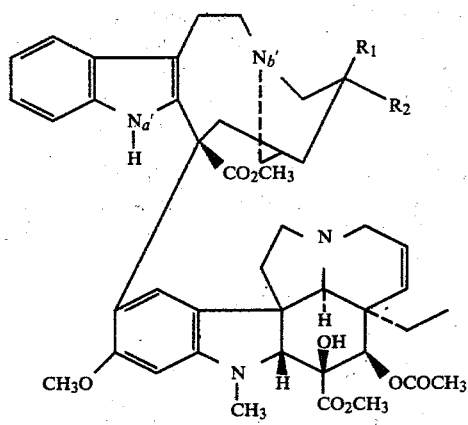

I wherein
leurosidine corresponds to: $R_1=C_2H_5$, $R_2=OH$; and
vinblastine corresponds to: $R_1=OH$, $R_2=C_2H_5$.

These alkaloids can be isolated from several species of Catharanthus, in particular C. roseus. However, these alkaloids, which have remarkable anti-tumour properties, are only present in small quantities in plants, and it is also particularly worthwhile to be able to prepare these compounds by partial synthesis from more abundant alkaloids.

The present invention thus provides a process for the preparation of a compound corresponding to formula (I), as defined above, by hydroxylation and reduction of $\Delta^{20'}$ dehydroxy-20'-vincaleucoblastine corresponding to formula (II):

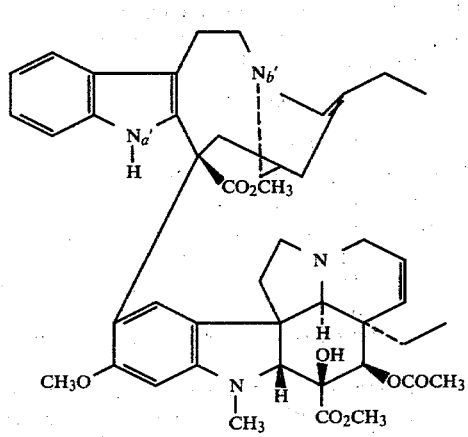

II

In a preferred embodiment of the process according to the present invention, the compound of formula (I), wherein $R_1$ is the hydroxy radical and $R_2$ is the ethyl radical and which is called vinblastine, is prepared by hydroxylation of the $\Delta^{20'}$ dehydroxy-20'vincaleucoblastine in a solvent in the presence of a metallic salt, followed by reduction of the product thus obtained by an alkali metal borohydride.

Suitable metallic salts include more particularly trivalent thallium salts, divalent mercury salts and tetravalent lead salts, particularly in the form of organic acid salts, especially carboxylic acid salts. Trivalent thallium acetate and trivalent thallium trifluoroacetate are mentioned particularly as preferred metallic salts.

Hydroxylation is preferably carried out in a chlorinated solvent such as dichloromethane.

The hydroxylation reaction may be carried out at ambient temperature, preferably with stirring and under an argon atmosphere, for a few hours.

Another embodiment of the process according to the present invention comprises preparing the compound according to formula (I), wherein $R_1$ is the ethyl radical and $R_2$ is the hydroxy radical, which compound is called leurosidine. In this process, the $\Delta^{20'}$ dehydroxy-20'-vincaleucoblastine is hydroxylated in a solvent by an electrophilic hydroxylation reagent, and the product thus obtained is reduced by an alkali metal borohydride.

Osmium tetroxide is mentioned as a particularly suitable electrophilic hydroxylation reagent. Osmium tetroxide can be used in a stoichiometric quantity or in a catalytic quantity, but in the present case it is necessary to provide an aliphatic or alicyclic tertiary amine N-oxide in the reaction medium. Where the osmium tetroxide is used in a stoichiometric quantity, this reagent has to be eliminated, for example by bubbling hydrogen sulphide into the mixture; where the osmium tetroxide is used in a catalytic quantity, it does not have to be eliminated.

In this embodiment of the process according to the present invention, hydroxylation is preferably carried out in a solvent such as an ether, for example diethyl ether or tetrahydrofuran.

The reduction stage of the process according to the present invention is preferably carried out in the presence of an alkali metal borohydride, for example sodium borohydride, and preferably in a hydroxylated solvent, for example methanol or ethanol.

This reduction is carried out at a temperature of between $-5°$ and $+5°$ C., preferably at $0°$ C.

In a preferred embodiment of the process according to the present invention, the $\Delta^{20'}$ dehydroxy-20' vincaleucoblastine is prepared by the action of an immonium-ion-forming reagent on dehydroxy-20' leurosidine $N_b'$-oxide of formula (III):

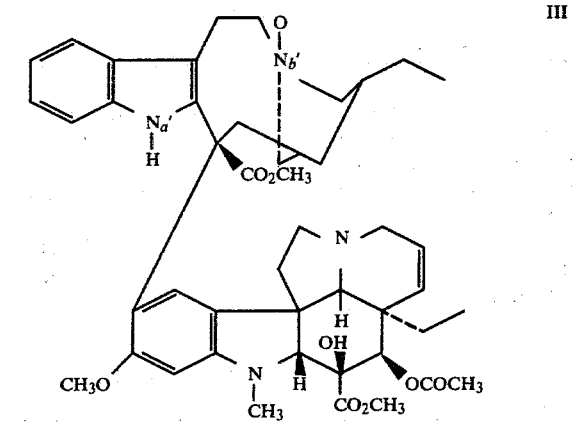

III

The immonium-ion-forming reagents are particularly organic or inorganic acid halides or anhydrides, particularly optionally halogenated carboxylic acid halides or anhydrides, and acetic anhydride should particularly be mentioned here.

In a preferred embodiment of the process, the $N_b'$-oxide in solution in an organic solvent such as dichloromethane is treated with acetic anhydride at a temperature of from $-5°$ to $+5°$ C. in order to produce the $\Delta^{20'}$ dehydroxy-20' vincaleucoblastine.

The $N_b'$-oxide may be prepared by known processes from dehydroxy-20'leurosidine, particularly by the action of an organic peracid according to the formula $R\text{-}CO_3H$ wherein R is an unsubstituted or substituted alkyl radical or aryl radical, the solvent which is used preferably being chosen from dichloromethane, chloroform or 1,2-dichloroethane. Peracids according to the formula $R\text{-}CO_3H$ which may be used in the operation of this stage of the process according to the present invention include, for example p-nitroperbenzoic acid, m-chloroperbenzoic acid and peracetic acid.

Dehydroxy-20' leurosidine may be prepared from dehydroxy-20' $\Delta^{15'}$ vincaleucoblastine, also called anhydro-vinblastine, by hydrogenating this compound. The hydrogenation of anhydrovinblastine may be carried out catalytically, for example by the use of a transition metal such as palladium on carbon suspended in an organic solvent such as ethanol, under a hydrogen atmosphere.

Anhydrovinblastine is a known product and a process for the partial synthesis thereof has been recently described in French Pat. No. 74 43221, filed on Dec. 30, 1974 in the name of l'Agence Nationale de Valorisation de la Recherche (ANVAR).

This partial synthesis of anhydrovinblastine starts from two known alkaloids, these being catharanthine and vindoline. Thus, the present invention makes possible the synthesis of vinblastine from two alkaloids which can be found fairly abundantly in nature.

The following reaction scheme summarizes the synthesis according to the present invention:

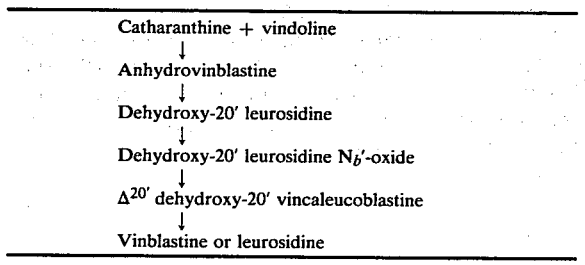

Naturally, the process according to the present invention generally results in the production of a mixture of products, from which leurosidine or vinblastine is isolated by known processes, particularly by chromatography.

The following Examples are given by way of example and naturally are not intended to limit the present invention in any way.

EXAMPLE 1

Preparation of dehydroxy-20' leurosidine

10% (10 mg) of palladium on carbon are added to a solution of 100 mg of $\Delta^{15'}$ dehydroxy-20' vincaleucoblastine in 5 ml of ethanol. The reaction medium is stirred for 12 hours under a hydrogen atmosphere.

After being filtered off on a glass fibre filter, the reaction medium is evaporated under vacuum and dehydroxy-20' leurosidine is thereby produced quantitatively.

EXAMPLE 2

Preparation of dehydroxy-20' leurosidine $N_b'$ oxide 22 mg of m-chloroperbenzoic acid are added to a solution of 100 mg of dehydroxy-20' leurosidine in 5 ml of dry dichloromethane under a nitrogen atmosphere and with stirring. After 10 minutes, the solution is extracted by 50 ml of chloroform and is washed 3 times with a solution of sodium bicarbonate in water (40 g/l)(three 5 ml portions). After being dried over sodium sulphate, followed by filtration and evaporation, dehydroxy-20' leurosidine $N_b'$-oxide is obtained quantitatively.

EXAMPLE 3

Preparation of leurosidine

150 µl of acetic anhydride are added with stirring to a solution of 50 mg of dehydroxy-20' leurosidine $N_b'$-oxide in 1 ml of dichloromethane at 0° C. After 3 hours, the reaction medium is evaporated to dryness under vacuum, and is absorbed by a mixture of 1 ml of tetrahydrofuran and 0.1 ml of pyridine, then treated at $-78°$ C. with a solution of 17 mg of osmium tetroxide in 0.1 ml of tetrahydrofuran.

The reaction medium is stirred for 12 hours at $-78°$ C. and is then absorbed by a solution of dichloromethane and ethanol in a ratio of 50:50 at ambient temperature. A stream of hydrogen sulphide is introduced into the reaction medium for 10 minutes, and the reaction medium is then filtered on glass fibre paper under vacuum, evaporated to dryness, absorbed by 2 ml methanol and reduced at 0° C. by excess sodium borohydride with stirring. The reduced reaction medium is extracted by 50 ml of chloroform, washed with water saturated with sodium chloride (two 10 ml portions), dried by sodium sulphate, filtered and evaporated under vacuum. Leurosidine which is thus obtained is separated from other reaction products by chromatography on a thick bed of silica (eluent: $CHCl_3$-MeOH 80/20).

EXAMPLE 4

Preparation of vinblastine

150 µl of acetic anhydride are added to a solution of 50 mg of dehydroxy-20' leurosidine $N_b'$-oxide in 1 ml of dichloromethane at 0° C. with stirring. After 3 hours, the reaction medium is evaporated to dryness under vacuum and treated with a solution of 50 mg of thallium triacetate in 2 ml of dichloromethane at ambient temperature with stirring and under an atmosphere of argon for 3 hours.

The reaction medium is evaporated under vacuum, absorbed by 2 ml of methanol and reduced by excess sodium borohydride. After being reduced, the reaction medium is extracted by 50 ml of chloroform, washed with water saturated with sodium chloride (two 10 ml portions), dried over sodium sulphate, filtered and evaporated under vacuum. The vinblastine thus obtained is separated from other reaction products by chromatography on a thick bed of silica (eluent: ACOEt-MeOH 90/10).

We claim:

1. A process for the preparation of vinblastine, which comprises hydroxylating Δ²⁰′ dehydroxy-20′ vincaleucoblastine according to formula (II):

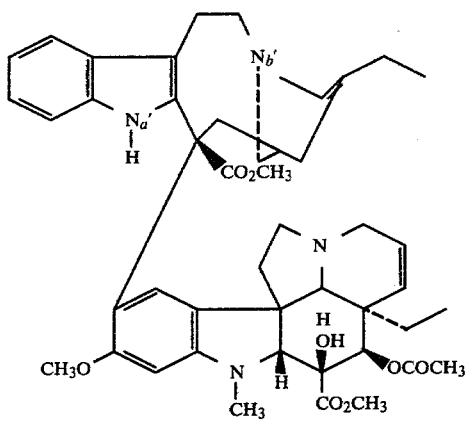

II in a solvent in the presence of a metallic salt selected from the group consisting of acetate and trifluoroacetate of Tl⁺³, Hg⁺⁺ and Pb⁺⁴, and reducing the compound which is obtained.

2. A process according to claim 1, wherein hydroxylation is carried out in a chlorinated solvent.

3. A process according to claim 2, wherein the chlorinated solvent is dichloromethane.

4. A process for the preparation of vinblastine according to any one of claims 1, 2 and 3, wherein said Δ²⁰′ dehydroxy-20′ vincaleucoblastine is prepared by the action in a solvent of an immonium-ion-forming agent on dehydroxy-20′ leurosidine N$_b$′-oxide according to formula (III):

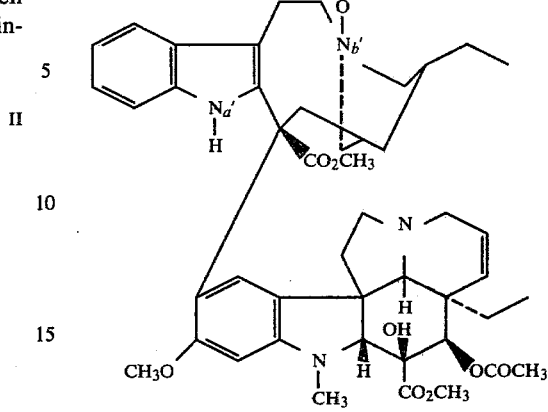

III

5. A process according to claim 4, wherein said immonium-ion-forming agent is a carboxylic acid anhydride.

6. A process according to claim 5, wherein said dehydroxy-20′ leurosidine N$_b$′-oxide is treated with acetic acid anhydride in dichloromethane at a temperature of from −5° to +5° C.

7. A process according to claim 4, wherein said dehydroxy-20′ leurosidine is treated with a reagent selected from the group consisting of m-chloroperbenzoic acid, p nitroperbenzoic acid and peroxyacetic acid, in a solvent selected from the group consisting of dichloromethane, chloroform, or dichloro-1, 2-ethane.

8. A process according to claim 1, wherein the reduction is carried out by an alkali metal borohydride.

9. A process according to claim 8, wherein the reduction is carried out in methanol or ethanol.

10. A process according to claim 1, wherein the reduction is carried out at 0° C.

* * * * *